United States Patent [19]
Kurtz et al.

[11] 3,941,568
[45] Mar. 2, 1976

[54] APPARATUS FOR THE PRODUCTION OF ETHYLENE DICHLORIDE

[75] Inventors: Bruce E. Kurtz, Marcellus; Anatoli Omelian, Jordan, both of N.Y.

[73] Assignee: Allied Chemical Corporation, New York, N.Y.

[22] Filed: July 15, 1974

[21] Appl. No.: 488,627

Related U.S. Application Data

[62] Division of Ser. No. 145,145, May 20, 1971, Pat. No. 3,839,475.

[52] U.S. Cl. .................................. 23/260; 23/263
[51] Int. Cl.² .................... B01J 1/00; C07C 17/02
[58] Field of Search ...... 23/260, 288 H, 288 K, 284, 23/263; 260/660

[56] References Cited
UNITED STATES PATENTS

| | | | |
|---|---|---|---|
| 2,098,148 | 11/1937 | Jarl | 23/288 H |
| 2,444,661 | 7/1948 | Maude | 260/660 |
| 2,547,139 | 4/1951 | Randall | 260/660 X |
| 2,929,852 | 3/1960 | Benedict | 260/660 |
| 3,255,161 | 6/1966 | Cobb, Jr. | 23/253 R X |
| 3,482,948 | 12/1969 | Miegel | 23/288 R |
| 3,502,443 | 3/1970 | Westerlund | 23/260 X |
| 3,527,820 | 9/1970 | Mercier | 23/260 X |
| 3,532,763 | 10/1970 | Stewart et al. | 260/660 X |

*Primary Examiner*—Joseph Scovronek
*Assistant Examiner*—Arnold Turk
*Attorney, Agent, or Firm*—Gerhard H. Fuchs

[57] ABSTRACT

Apparatus for making ethylene dichloride by reacting ethylene and chlorine in liquid reaction medium includes a reaction zone having gas inlets for the ethylene and chlorine at the lower portion thereof, the reaction zone being connected by conduits to externally located indirect heat exchange means so as to provide a path for continuous circulation of the liquid reaction medium through the reaction zone and the heat exchange means caused by thermosyphon effect generated by heat of reaction and/or the gas-lift effect induced by the introduction of the reactants. The reaction zone has a vapor outlet at the upper portion thereof in communication with condenser means for condensing vaporous ethylene dichloride product to recover liquid ethylene dichloride.

6 Claims, 1 Drawing Figure

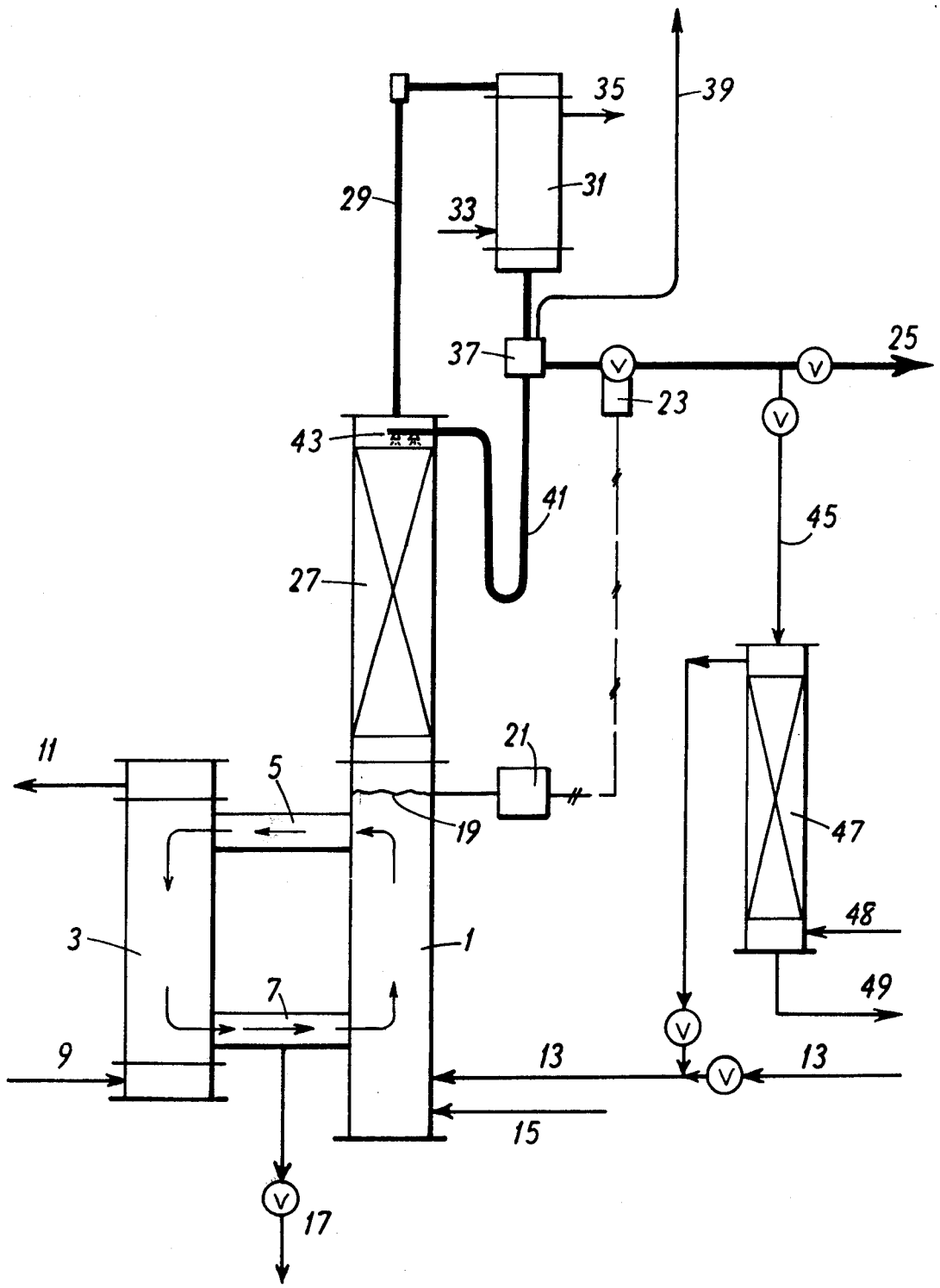

APPARATUS FOR THE PRODUCTION OF ETHYLENE DICHLORIDE

This is a division, of application Ser. No. 145,145, filed May 20, 1971, and now U.S. Pat. No. 3,839,475.

BACKGROUND OF THE INVENTION

1. Field of the Invention

This invention relates to an improved process for preparing ethylene dichloride (1,2-dichloroethane). More particularly, the invention relates to an improved method whereby substantially pure ethylene dichloride is prepared by the liquid phase reaction between ethylene and chlorine. Ethylene dichloride has many uses, not the least of which is as raw material in the manufacture of vinyl chloride.

Most present-day commercial processes for the production of ethylene dichloride, as well as the modified process of the present invention, are based on the liquid phase reaction between ethylene and chlorine within a body of liquid ethylene dichloride. The reaction between chlorine and ethylene is highly exothermic and the temperature in the reaction medium must be controlled to prevent the formation of substitution reaction products which limit the value of the ethylene dichloride product for certain commercial processes and particularly for its use in the production of vinyl chloride by pyrolysis.

2. Description of the Prior Art

U.S. Pat. No. 2,393,367 discloses a procedure for the preparation of ethylene dichloride wherein ethylene and chlorine are introduced into a water-cooled reactor containing ethylene dichloride with a small amount of ferric chloride as a substitution reaction depressant. The reactor employed is constructed with a plurality of internal tubes which carry a cooling agent to thereby maintain the reaction medium at a temperature of about 40° C., which is well below the boiling point of ethylene dichloride (83.5° C.). As reported, at least about 0.5% of the chlorine added reacts by substitution to form undesired higher chlorinated products. The product provided by this process would therefore require various purification steps before achieving suitability as a raw material for the production of vinyl chloride, as well as for many other uses to which it might be put. The primary contribution of this expired patent to the art is the use of ferric chloride to depress the unwanted substitution reactions and thereby reduce the degree of contamination of the final product with undesirable highly chlorinated substitution products.

U.S. Pat. No. 2,929,852 also discloses a modified process directed to the liquid phase reaction between ethylene and chlorine. In this disclosure, ethylene dichloride is not only the product but serves as the reaction medium as well, and direct temperature control is achieved by utilizing the exothermic heat of reaction to vaporize that portion of the ethylene dichloride which becomes the purified product. The temperature of the reaction medium is held between 80° and 120° C. at pressures between 0 and 25 lbs. per square inch gauge (psig). The vaporized portion of the ethylene dichloride reaction medium is conducted to a rectification column. Ethylene dichloride is separated from the higher chlorinated reaction products and the ethylene dichloride product is removed in liquid phase from the rectification zone. The product of this process, although of greater purity than that obtainable from the process of U.S. Pat. No. 2,393,367 previously cited, nevertheless is less pure than the product of the present invention.

We have now found surprisingly, in contrast to the teachings of the prior art, that the method of controlling the exothermic reaction by circulating the reaction medium through an external heat exchanger, in combination with the method of removing heat from the reaction medium by the continuous vaporization of a portion of said reaction medium to thus maintain the temperature from 83° C. to higher temperatures depending on the quantity of high boilers present, preferably between 83° to 90° C., has an appreciable and beneficial effect on the degree of purity of the final ethylene dichloride product. We have found the method of the present invention to be superior in this respect, to the methods of control involving internal coolers, or cooling exclusively, by utilization of the heat of vaporization of a volatile reaction medium.

In the production of vinyl chloride by pyrolysis, not only is the assay of the ethylene dichloride raw material important, but the nature of its impurities as well. Certain chlorinated contaminants such as ethyl chloride and 1,1,2-trichloroethane are especially detrimental when present, even in minute quantities. For this reason, it has heretofore generally been necessary, regardless of the manner of preparation of the ethylene dichloride, to subject it to costly purification steps before it could be pyrolyzed for the production of vinyl chloride. The product of the process of the present invention, however, is essentially free of chlorinated substitution reaction products including ethyl chloride, 1,1,2-trichloroethane and other undesirable contaminants and therefore said process may be employed in the production of high quality vinyl chloride by pyrolysis, without further purification.

SUMMARY OF THE INVENTION

Ethylene dichloride is produced in accordance with the present invention by conducting the liquid phase reaction of ethylene with chlorine in a circulating body of ethylene dichloride as a reaction medium, utilizing the exothermic heat of reaction to vaporize a portion of the liquid ethylene dichloride reaction medium, and controlling the rate of vaporization of the reaction medium primarily by means of an external cooler through which the hot reaction medium is permitted to circulate. The hot reaction medium circulates from the bottom of the reaction or vaporization zone to the top, then to the top of the cooling or heat extraction zone, then to the bottom of the heat extraction zone and then back into the bottom of the reaction zone, thus describing a continuous cyclic loop.

A portion of the exothermic heat of reaction is thus removed, which portion would otherwise be expanded in additional vaporization of the reaction medium. Control of the quantity of heat removed and accordingly, control of the rate of vaporization is had, primarily by varying the temperature and/or the amount of coolant passing through said heat exchanger. A small quantity of the reaction medium is generally purged from the circulating system, either continuously or periodically, in an amount sufficient to prevent a buildup of highly chlorinated substitution reaction products in said reaction medium. Although the quantity of said substitution reaction products produced by the process of the present invention is remarkably low, the higher boiling products among them are not otherwise removed. If permitted to accumulate in the reaction medium, these undesirable by-products would eventually build up enough to provide some carry-over into the final product, which would then require further purification. Ethyl chloride and 1,1,2-trichloroethane are particularly detrimental to an ethylene dichloride product which is to be used as raw material for the production of vinyl chloride. Ethyl chloride, being a low boiling by-product (B. Pt. 12.3° C.) is generally vented along with any non-condensibles, but 1,1,2-trichloroethane being a relatively high boiling by-product (B. Pt. 113.5° C.) accumulates in the reaction medium. The amount of 1,1,2-trichloroethane that can be tolerated in the reaction medium without jeopardizing the quality of the product ethylene dichloride is correlated with the efficiency of the rectification section discussed below, thus a higher weight-percent of this undesirable by-product can be tolerated where the rectification section chosen is highly efficient.

We have found that a high purity ethylene dichloride product can be obtained, substantially free of 1,1,2-trichloroethane and other undesirable by-products, by our cyclic process involving as a feature, purging to maintain the quantity of these by-products in the circulating liquid body at a low level, preferably below 10%, desirably below 5%.

As a guide, the amount purged should be chosen so as to contain an amount of 1,1,2-trichloroethane substantially equal to or greater than the amount of this chlorinated compound produced in the same unit time as by-product. Generally, the quantity purged amounts to about 1 to 10% of the weight of the product ethylene dichloride withdrawn. The ethylene dichloride in this purged material can be subsequently recovered by distillation, and recycled.

In the process of our invention, the ethylene dichloride vapors from the reactor are conducted to a rectification section. The ethylene dichloride vapor which leaves the rectification section is condensed and the liquid ethylene dichloride is separated from the small quantity of non-condensible side reaction products which are formed along with the ethylene dichloride. Generally, the greater portion of the condensed ethylene dichloride is returned to the rectification section as reflux in an amount sufficient to provide a reflux ratio of at least 0.5:1, preferably 1:1 to 6:1, and the balance is withdrawn as high purity ethylene dichloride product.

It has been found, surprisingly, that controlling the rate of vaporization of the reaction medium by using an external cooler through which the medium circulates, appreciably improves the purity of the final ethylene dichloride product.

It may be asked why the external heat exchange zone of this invention provides a purer product than may generally be obtained with internal cooling, or with full reliance on the heat of vaporization of the reaction medium, for the absorption of heat. The external heat extraction zone not only controls the rate of vaporization, but is responsible as explained below, for the intimate mixing of ethylene and chlorine which is essential to the production of a high purity ethylene dichloride. The heat extraction or heat exchange zone in combination with the reaction zone produces a continuous loop or cyclic system through which the reaction mixture may circulate to form a co-current flow of the reaction medium and the reactants. Whereas this circulation may be produced or accelerated by mechanical means, we find that the thermosyphon effect, coupled with the gas-lift effect induced by the introduction of the reactants, the heat of reaction, and the bubbles of vapor produced thereby, is sufficient to provide the circulation required.

The desired reaction between the chlorine and ethylene we believe takes place at the gas-liquid interface, while the side reactions are thought to take place in the gas phase. For this reason, good dispersion of the reactants, which is associated with a relatively large area of gas-liquid interface, is important for a high product yield coupled with a low yield of the undesirable side reaction products. To that end, the ethylene and chlorine inlets may include sparging means for distributing gases passing therethrough in small discrete bubbles.

As previously emphasized, this reaction is highly exothermic. When the reactants are mixed in a reaction vessel without benefit of an external heat exchange zone, large bubbles of vapor are formed as the vapor pressure of the mixture reaches ambient pressure. Such large bubbles provide relatively little gas-liquid interface throughout the reaction medium, and therefore a relatively large yield of undesired side reaction products. In comparison, the co-current flow made possible by the use of the external heat exchanger of the present invention, and the good dispersion that results therefrom, provides a preponderance of very small bubbles of vapor. Consequently, a large area of gas-liquid interface is obtained, and correspondingly, a favorable ratio of ethylene dichloride product to side reaction by-products. As is well known, the surface area of a large number of small bubbles is much greater than the surface area of fewer large bubbles of equivalent volume.

The method of our invention provides for the rectification of the vaporized reaction medium, and also for the continuous withdrawal of the products of the reaction and the recovery of an ethylene dichloride substantially free of reaction side products.

The temperature at which the reaction is conducted should be the boiling point of the circulating liquid body, which constitutes the reaction medium. At atmospheric pressure, the boiling point will range from 83.3° C. (the boiling point of pure ethylene dichloride), to higher temperatures depending on the quantity of high boilers present. Typical reaction temperatures are 83°–90° C. It is, of course, possible to carry out the reaction at pressures somewhat above and below atmospheric pressure with a corresponding shift in the boiling range, but nothing is gained thereby.

To prevent the accumulation of high boiling impurities which form in the reaction as a result of substitution reactions, an amount of the reaction medium corresponding to between 1 and 10% of the weight of the product ethylene dichloride is purged from the body of circulating liquid. Obviously, there will be a correlation between the amount purged and the boiling point of the reaction medium. If too little of the reaction medium is purged, the quantity of high boiling impurities in the reaction medium will gradually increase, with a corresponding increase in the boiling point of the mixture.

Ferric chloride can be added to the reaction medium as a catalyst to depress the reaction rate of the substitution reactions. $Fe^{+++}$ should be present in the reaction medium, to the extent of at least 50 parts per million (ppm), preferably to the extent of about 500–2000 ppm. Iron or steel equipment can be used for this reaction, and when it is, a trace of iron will generally be picked up by the reaction medium as a result of superficial corrosive action. If the ferric ion already present in the reaction medium is less than 500 ppm, a quantity of ferric chloride is added to bring the $Fe^{+++}$ content preferably to at least 500 ppm.

A small amount of oxygen can also be added to the reaction mixture to further inhibit by-product formation. Oxygen is particularly effective in repressing the formation of 1,1,2-trichloroethane. The oxygen is preferably added with the chlorine in the amount of about 0.5% by weight, based on the chlorine. Air may be introduced with the chlorine in place of pure oxygen to an extent sufficient to provide the chlorine with an equivalent percent of oxygen.

In preparing ethylene dichloride by the process of the present invention, the reactants may be supplied to the circulating ethylene dichloride reaction medium in stoichiometric amounts. However, it is preferred that the reactants be supplied in such proportions as to provide an excess of ethylene over and above the stoichiometric amount required to react with the added chlorine to prepare ethylene dichloride. When this detail is observed, the tendency for substitution reactions to develop during the process, is markedly reduced. While the amount of excess of the ethylene is not critical, the preferred mole ratio of $Cl_2$ to $C_2H_4$ lies between 0.9 and 0.95 to 1.

The process of the present invention can be conducted in a reactor provided with a rectification or fractionating zone. Such a rectification zone may comprise any fractionating column designed to provide good liquid-vapor contact. Such a column will increase the purity of the existing ethylene dichloride vapor by separating and recycling to the reactor any high boiling side reaction products produced by the reaction. The equipment employed is not critical, but it should have reasonable resistance to corrosion from the reactants and from the reaction products. As previously mentioned, steel equipment is generally satisfactory. The rectification zone of the reactor may comprise a series of bubble cap trays or sieve plates, or it may comprise a column packed with Rashig rings, saddles or other suitable packing normally employed in rectification equipment. The specific structure and other details of the rectification zone actually employed may be readily determined by those familiar with rectification procedures. As might be expected, increasing the height of the rectification zone increases the purity of the ethylene dichloride product.

The invention may be further described with reference to the drawing which diagrammatically illustrates the preferred equipment which may be employed in carrying out the process.

A reactor 1 is provided with a heat extraction zone or heat exchanger 3, through which ethylene dichloride as the circulating liquid body or reaction medium may circulate by entering through conduit 5, and returning through conduit 7. Conduits, or liquid transfer means, 5 and 7 should preferably have effective inside diameters sufficiently large to permit adequate circulation of the reaction medium through the cyclic system formed by reactor 1, heat exchanger 3, and the interconnecting conduits 5 and 7. In order to permit good circulation of the reaction medium the effective cross-sectional area of the heat exchanger should desirably be no less than about the cross-sectional area of the conduits, and the cross-sectional area of said conduits should be no less than about 2% of the cross-sectional area of the reaction zone. Preferably, the cross-sectional area of the conduits should be about 15 to 100% of the effective cross-sectional area of the reaction zone. Both conduits should be positioned entirely below the surface of the reaction medium when the equipment is operating, but one (5) should connect reactor and heat exchanger at points near and just below the liquid surface, and the other (7) at a point in the lower portion of the reactor. In the preferred embodiment, this heat exchanger is water cooled, the cooling water inlet and outlet being shown as 9 and 11 respectively. The lower portion of reactor 1 comprises the reaction section and is provided with an inlet 13 for raw material ethylene, and inlet 15 for chlorine gas containing about 0.5% by weight of oxygen (or a quantity of air sufficient to provide this quantity). Outlet 17 at a low point in the reactor system is provided for purging the system.

The level of the ethylene dichloride reaction medium is maintained at 19 by level controller 21 which performs its function by controlling valve 23, thus policing the amount of ethylene dichloride product which is continuously withdrawn at 25.

Reactor 1 is also provided at the upper end thereof with a rectification section 27, from the top of which the ethylene dichloride and any low boiling substitution reaction products leave as vapors through riser 29 and enter the upper vestibule of downcoming condenser 31. Cooling water is admitted to the jacket of condenser 31 through inlet 33 and outlet 35. The condensate and non-condensibles leaving the condenser enter separator 37 from which the non-condensibles are vented through vent line 39. At the separator the condensate is split into two streams, one being returned through lute 41 and sparger 43 to the top of the rectification section, as reflux. The other stream, passing through control valve 23, leaves at point 25 as purified ethylene dichloride. The variable positioning of valve 23, manually or automatically, in response to signals from level-sensing device 21, will maintain the level in the reactor by controlling the product flow at 25 or 49 and thus the amount of reflux (generally the larger portion of the condensate), through lute 41 to sparger 43 and column 27. This action is facilitated when overflow line 41 extends a short distance up into separator 37 and is protected from the direct stream from condenser 31 by off-set positioning, by a protecting hood, a crooked end or other means. For example, if level 19 drops below a pre-selected point, sensing means 21 causes valve 23 to partially close. More condensate then accumulates in separator 37 and overflows through lute 41 to column 27, thence back to reactor 1, raising the liquid level at 19. If the liquid level 19 rises above the pre-selected point, sensing means 21 causes valve 23 to open further. This increases the rate of product withdrawal, and decreases the amount of reflux (condensate return to the reactor), thereby lowering the liquid level as the distillation progresses. The liquid level choses in generally several inches above the upper interconnection between the reactor and heat exchanger to insure uninterrupted circulation of the liquid through the cyclic system.

When the reactants are fed at a constant rate through lines 13 and 15, the amount of condensate from condenser 31 can be controlled by varying the amount of, or the temperature of, the coolant applied to the jacket of heat exchanger 3. Decreasing the rate of flow of the coolant, or increasing its temperature reduces the quantity of heat being removed from the reaction mixture, leaving more to be expended in vaporizing the product and reaction medium, and consequently increasing the amount of total condensate. With this arrangement, then, it follows that the reflux ratio can be governed by the degree of cooling provided by the external heat exchanger 3.

The product ethylene dichloride obtained at point 25 is of excellent quality for the production of vinyl chloride by pyrolysis, but it may contain a trace of hydrogen chloride which might be objectionable for general sales. This trace of HC1 can be scrubbed out by passing the product through line 45 to packed column 47 countercurrent to the stream of incoming raw material ethylene which enters at 48. HC1-free, high purity, ethylene dichloride would then be withdrawn at 49. In this circumstance, the inconsequential amount of hydrogen chloride carried by the ethylene feed to reactor 1 would eventually be vented at line 39.

To prepare ethylene dichloride by the preferred process of this invention, fill reactor 1 and attached heat exchanger 3 with dry ethylene dichloride to level 19, to be maintained thereat by level controller 21. Add ferric chloride to this reaction medium to provide between 500 and 2000 ppm of iron based on the total charge. Sweep the system with ethylene, then slowly sparge ethylene into the bottom of reactor 1 through line 13, and chlorine gas containing about 0.5% oxygen or an amount of air to provide a corresponding amount of oxygen, through line 15. The ethylene should be added in slight excess, the mole ratio of chlorine being between 0.90 to 0.95 per mole of ethylene. Continue the addition of the reactants, gradually increasing the rate, until the reaction medium reaches its boiling point (83.3° C. or higher, depending on the quantity of high boiling impurities that are present). Adjust the rate of addition of the reactants, and the amount of cooling water to heat exchanger 3, so as to obtain adequate reflux without flooding the rectification zone 27 or exceeding the capacity of condenser 31. At point 17 in the reaction system, continuously purge a portion of the reaction medium equal to between 1 and 10% of the product rate. The precise rate of purge will be adjusted by experience, to that which will maintain the amount of undesirable highly chlorinated substitution reaction products in the reaction medium at a satisfactory low level. A "satisfactory" level may be defined as one consistent with an ethylene dichloride product of acceptable purity. The ethylene dichloride purged can be recovered by distillation. The ethylene dichloride product obtained by the process of the present invention can be diverted directly to cracking furnaces, if it is to be used for vinyl chloride production by the pyrolysis route. The ethylene dichloride product may contain a trace of hydrogen chloride, however, which may lessen its value for certain other uses. If the product is to be free of HC1, it may be passed downwardly through packed column 47 countercurrent to the flow of incoming ethylene raw material, which is diverted through said column enroute to the reactor. Such a stream of ethylene will sweep the ethylene dichloride essentially free of HC1. The negligible amount of HC1 picked up by the ethylene is not detrimental to the $C_2H_4/Cl_2$ reaction and essentially all of it is removed with the non-condensibles at 37, then vented through vent line 39.

EXAMPLE 1

Small scale equipment is set up corresponding to the equipment arrangement of FIG. 1, using an iron reactor. The reactor consists of a length of iron pipe 3 feet 4 inches long, having an inside diameter (ID) of 4 inches. Gas inlets enter the reactor near the bottom and these are equipped with sparging means for the dispersion of the reactant gases. A drain cock is also provided at the bottom for purging the system. A jacketed iron tubular heat exchanger having an overall diameter of 6 inches and a length of 3 ½ feet is positioned parallel and adjacent to the reactor. The heat exchanger is connected to the reactor by two 2 inches ID iron pipes at two points. One is centered at a point 4 inches from the bottom of the reactor, and extends horizontally to the outlet vestibule of the heat exchanger. The second is centered at a point 4 inches from the top of the reactor and extends horizontally to the inlet vestibule of the heat exchanger. A cyclic system is thereby formed, suitable for the cyclic flow of a reaction medium therein. The reactor system as illustrated diagrammatically in FIG. 1 is charged with 14 liters of ethylene dichloride (as the reaction medium) bringing the liquid level just above the upper interconnection between the reactor and heat exchanger. A small amount of ferric chloride is added (25 grams, anhydrous basis) to provide a $Fe^{+++}$ content of about 500 ppm based on the weight of the ethylene dichloride charge. Before any chlorine is added, the system is first purged with ethylene as a safety measure, since, as previously emphasized, the reaction between ethylene and chlorine is highly exothermic. The presence of air in the system at the start could conceivably produce an explosive condition. (An inert gas can be used at this point if desired.) The feed ethylene, chlorine and oxygen (air) are accurately measured by means of suitable flow meters. The following rates of addition are employed:

Chlorine, 60 grams per minute
Ethylene, 26.1 grams per minute
Air, 0.58 grams per minute This represents a mole ratio of chlorine to ethylene of 0.91 to 1.0. The operation is carried out essentially at atmospheric pressure. The reactor temperature is maintained at 84° C., and the ethylene dichloride product is withdrawn at the rate of about 75 grams per minute, while about 4 grams per minute of ethylene dichloride are purged from the reactor system, thus maintaining the quantity of substitution reaction products which may accumulate in the reaction medium at a low and essentially constant level.

The reflux ratio is maintained at about 5.4 to 1.0. 96–99% of the chlorine is converted to ethylene dichloride.

The purity of the product obtained is found to be 99.80% ethylene dichloride, which is exceptionally high for this material.

EXAMPLE 2

Example 2 is carried out exactly as was Example 1, with the exception that no ferric chloride is added, since the reaction medium from Example 1, which already contained $Fe^{+++}$ was reused. Furthermore, a slight corrosive attack of the wall of the iron reactor had increased the $Fe^{+++}$ content to some degree, totaling between 500 and 1000 ppm. The reactor temperature is maintained at 86° C. Feed rates, reflux ratio, and product and purge rates are the same. The purity of the product is 99.74%

EXAMPLE 3

Example 3 is carried out exactly as was Example 1, with the sole exception that the conduits to the external heat exchanger are blanked off. Feed rates, reactor temperature, reflux ratio, ferric iron concentration and product and purge rates are the same. 96–98% of the chlorine is converted to ethylene dichloride. The product is found to assay 99.36% ethylene dichloride. It will be noted that there is a decrease in product purity of about 0.44% when external means of cooling, with the associated circulation of the reaction medium, are not provided.

EXAMPLE 4

Example 4 is carried out exactly as was Example 3. No make-up ferric chloride is required, as the $Fe^{+++}$ content is 500 to 1000 ppm resulting from slight attack of the reactor. Feed rates, reactor temperature, reflux ratio, ferric iron concentration and product and purge rates are the same. 96–98% of the chlorine is converted to ethylene dichloride. The product is found to assay 99.17% ethylene dichloride. Again, it will be noted that a decrease in product purity occurs, this time amounting to almost 0.6%. when external means of circulating and cooling the reaction medium are not provided.

The degree of improvement in the purity of the ethylene dichloride product when circulation and external cooling of the reaction medium is provided, averages about 0.5%. This improvement is very significant. When product of this degree of purity is used in the production of vinyl chloride by pyrolysis, the vinyl chloride obtained is consistently of good quality and results are reproducible.

To summarize, the method of our invention comprises an efficient and economical continuous cyclic process which includes a method of purging, so as to maintain a substantially clean circulating body, and thus prevent build-up of chlorinated side reaction by-products in the body. The final high purity ethylene dichloride product requires no further purification treatment, and is suitable as raw material for the pyrolytic production of vinyl chloride as well as for other purposes where an ethylene dichloride product, free of chlorinated by-product contaminants is essential.

Other olefins, such as propylene, butylene and the like may also be chlorinated to their corresponding dichlorides by employing the process of this invention.

Various changes may be made in the details of operation and in the apparatus employed without departing from the invention or sacrificing any of the advantages thereof.

We claim:

1. Apparatus for making ethylene dichloride by reacting ethylene and chlorine in a liquid reaction medium of ethylene dichloride, comprising:
   a. a vertically disposed reaction vessel for effecting reaction between the ethylene and chlorine, having at least one inlet each for the ethylene and the chlorine positioned in the lower portion thereof, the reaction vessel having an upper outlet and a lower inlet for the reaction medium to be circulated therethrough, the upper outlet being located below the liquid level, the reaction vessel further having a vapor outlet located in the upper portion thereof above the liquid level;
   b. indirect heat exchange means located externally of the vertically disposed reaction vessel for removing heat of reaction from the reaction medium, the indirect heat exchange means having an upper inlet and a lower outlet for the reaction medium to be circulated therethrough;
   c. a conduit connecting the upper outlet of the reaction vessel with the upper inlet of the heat exchange means;
   d. a conduit connecting the lower inlet of the reaction vessel with the lower outlet of the heat exchange means;

to establish a path for continuous circulation of the reaction medium through the reaction vessel and the heat exchange means predominantly caused by the thermosyphon effect generated by heat of reaction and/or the gas-lift effect induced by introduction of the reactants; and further comprising
   e. condensor means in communication with the vapor outlet of the reaction vessel for condensing ethylene dichloride product vapor to recover liquid ethylene dichloride product; and
   f. conduit means associated with the condensor means for discharging condensed ethylene dichloride product from the apparatus.

2. Apparatus according to claim 1 wherein the reaction vessel has a rectification section at the upper end thereof.

3. Apparatus according to claim 2, additionally comprising conduit means connecting the condensor means with the rectification section to permit return of part of the condensed ethylene dichloride product from the condensor means to the rectification section of the reaction vessel as reflux.

4. Apparatus according to claim 1 wherein the effective cross-sectional area of the conduits is from 15 to 100% of the effective cross-sectional area of the reaction vessel, and the effective cross-sectional area of the indirect heat exchange means is not less than about the cross-sectional area of the conduits.

5. Apparatus according to claim 4 wherein the reaction vessel has a rectification section at the upper end thereof, and wherein part of the condensed liquid ethylene dichloride is returned to the rectification section in amount sufficient to provide reflux ratio of from 1:1 to 6:1.

6. Apparatus according to claim 5 wherein the chlorine and ethylene inlets include sparging means for distributing gases passing therethrough in small discrete bubbles.

* * * * *